US 9,267,114 B2

United States Patent
Yamshchikov

(10) Patent No.: US 9,267,114 B2
(45) Date of Patent: Feb. 23, 2016

(54) FLAVIVIRUS ENVELOPE PROTEIN MUTATIONS AFFECTING VIRION DISASSEMBLY

(71) Applicant: Southern Research Institute, Birmingham, AL (US)

(72) Inventor: Vladimir Yamshchikov, Birmingham, AL (US)

(73) Assignee: SOUTHERN RESEARCH INSTITUTE, Birmingham, AL (US)

( * ) Notice: Subject to any disclaimer, the term of this patent is extended or adjusted under 35 U.S.C. 154(b) by 0 days.

(21) Appl. No.: 13/671,111

(22) Filed: Nov. 7, 2012

(65) Prior Publication Data
US 2014/0127261 A1 May 8, 2014

(51) Int. Cl.
| | |
|---|---|
| *C12N 7/04* | (2006.01) |
| *C07K 14/005* | (2006.01) |
| *A61K 39/12* | (2006.01) |
| *C12N 7/00* | (2006.01) |
| *A61K 39/00* | (2006.01) |

(52) U.S. Cl.
CPC ............... *C12N 7/04* (2013.01); *C07K 14/005* (2013.01); *C12N 7/00* (2013.01); *A61K 39/00* (2013.01); *C12N 2770/24122* (2013.01); *C12N 2770/24162* (2013.01)

(58) Field of Classification Search
None
See application file for complete search history.

(56) References Cited

U.S. PATENT DOCUMENTS

| | | |
|---|---|---|
| 7,455,842 B2 | 11/2008 | Yamshchikov |
| 7,459,163 B2 | 12/2008 | Yamshchikov |
| 2004/0031072 A1 | 2/2004 | Larosa et al. |
| 2004/0123343 A1 | 6/2004 | Larosa et al. |
| 2005/0002968 A1 | 1/2005 | Monath et al. |
| 2005/0053624 A1 | 3/2005 | Arroyo et al. |
| 2005/0276816 A1 | 12/2005 | Yamshchikov et al. |
| 2007/0036827 A1 | 2/2007 | Khromykh et al. |
| 2007/0044171 A1 | 2/2007 | Kovalic et al. |
| 2007/0269458 A1 | 11/2007 | Guirakhoo et al. |
| 2009/0317409 A1 | 12/2009 | Xu et al. |
| 2010/0298233 A1 | 11/2010 | Pasqualini et al. |
| 2012/0201852 A1 | 8/2012 | Guirakhoo et al. |

OTHER PUBLICATIONS

GenBank: AFG28920.1, http://www.ncbi.nlm.nih.gov/protein/afg28920, dated Apr. 3, 2011.*
GenBank: ABI81248.1, http://www.ncbi.nlm.nih.gov/protein/114803791?report=genbank&log$=protalign&blast_rank=93&RID=R1PV0ZEJ01R, dated May 8, 2007.*
GenBank: AAK59268.1, http://www.ncbi.nlm.nih.gov/protein/14290129?report=genbank&log$=protalign&blast_rank=27&RID=RPTNSUDH015, dated Jun. 5, 2001.*
Mantel et al. Genetic stability of a dengue vaccine based on chimeric yellow fever/dengue viruses. Vaccine. Sep. 2, 2011;29(38):6629-35. doi: 10.1016/j.vaccine.2011.06.101. Epub Jul. 13, 2011.*
Porter et al. Immunogenicity and protective efficacy of a vaxfectin-adjuvanted tetravalent dengue DNA vaccine. Vaccine. Jan. 5, 2012;30(2):336-41. doi: 10.1016/j.vaccine.2011.10.085. Epub Nov. 12, 2011.*
Rothman et al. Induction of T lymphocyte responses to dengue virus by a candidate tetravalent live attenuated dengue virus vaccine. Vaccine. Sep. 14, 2001;19(32):4694-9.*
pcDNA3, http://www.synthesisgene.com/vector/pcDNA3.1%20Zeo(-).pdf, not dated.*
Konishi et al. Evidence for antigen production in muscles by dengue and Japanese encephalitis DNA vaccines and a relation to their immunogenicity in mice. Vaccine. Sep. 8, 2003;21(25-26):3713-20.*
GenBank: JQ317715.1. Dengue virus 1 isolate LD101-ZS2002 envelope protein gene, partial cds. http://www.ncbi.nlm.nih.gov/nuccore/JQ317715.1. Dated Apr. 3, 2012.*
Revised Version of International Search Report and Written Opinion dated Aug. 1, 2014 issued for related PCT application PCT/US2013/068616. (43 pgs).
Nybakken, G.E., et al., *Crystal Structure of the West Nile Virus Envelope Glycoprotein,* J. Virol., Dec. 2006, vol. 80, No. 23: pp. 11467-11474 (8 pgs), Fig. 1C.
Hahn, C.S., et al., *Comparison of the Virulent Asibi Strain of Yellow Fever Virus with the 17D Vaccine Strain Derived From It,* Proc. Natl. Acad. Sci. U.S.A., Apr. 1987, vol. 84, No. 7: pp. 2019-2023 (5 pgs), Fig. 5.
Mandl, C.W., et al., *Complete Genomic Sequence of Powassan Virus: Evaluation of Genetic Elements in Tick-Borne Versus Mosquito-Borne Flaviviruses,* Virology, May 1993, vol. 194, No. 1: pp. 173-184 (12 pgs); Figs. 1 & 3.
International Search Report and Written Opinion dated May 7, 2014 issued for related PCT application PCT/US2013/068616. (17 pgs).

* cited by examiner

*Primary Examiner* — Stacy B Chen
*Assistant Examiner* — Nick Zou
(74) *Attorney, Agent, or Firm* — Stinson Leonard Street LLP

(57) ABSTRACT

Mutations in the central monomer contact interface of the flavivirus envelope protein which modulate the infectivity of the flavivirus are made. The mutations decrease the ability of the envelope dimer protein to dissociate.

33 Claims, 3 Drawing Sheets

```
                       SEQUENCE LISTING

<160> NUMBER OF SEQ ID NOS: 10

<210> SEQ ID NO 1
<211> LENGTH: 5
<212> TYPE: PRT
<213> ORGANISM: Flavivirus
<220> FEATURE:
<221> NAME/KEY: MUTAGEN
<222> LOCATION: (1)..(5)
<223> OTHER INFORMATION: Mutation in central monomer contact interface
      of flavivirus envelope protein

<400> SEQUENCE: 1

Arg Ser Gln Glu Gly
1               5

<210> SEQ ID NO 2
<211> LENGTH: 5
<212> TYPE: PRT
<213> ORGANISM: Flavivirus
<220> FEATURE:
<221> NAME/KEY: MUTAGEN
<222> LOCATION: (1)..(5)
<223> OTHER INFORMATION: Mutation in central monomer contact interface
      of flavivirus envelope protein

<400> SEQUENCE: 2

Arg Asn Gln Glu Gly
1               5

<210> SEQ ID NO 3
<211> LENGTH: 5
<212> TYPE: PRT
<213> ORGANISM: Flavivirus
<220> FEATURE:
<221> NAME/KEY: MUTAGEN
<222> LOCATION: (1)..(5)
<223> OTHER INFORMATION: Mutation in central monomer contact interface
      of flavivirus envelope protein

<400> SEQUENCE: 3

Gly Asp Gln Thr Arg
1               5

<210> SEQ ID NO 4
```

```
<211> LENGTH: 5
<212> TYPE: PRT
<213> ORGANISM: Flavivirus
<220> FEATURE:
<221> NAME/KEY: MUTAGEN
<222> LOCATION: (1)..(5)
<223> OTHER INFORMATION: Mutation in central monomer contact interface
      of flavivirus envelope protein

<400> SEQUENCE: 4

Lys Ser Gln Glu Gly
1               5

<210> SEQ ID NO 5
<211> LENGTH: 5
<212> TYPE: PRT
<213> ORGANISM: Flavivirus
<220> FEATURE:
<221> NAME/KEY: MUTAGEN
<222> LOCATION: (1)..(5)
<223> OTHER INFORMATION: Mutation in central monomer contact interface
      of flavivirus envelope protein

<400> SEQUENCE: 5

Lys Asn Gln Glu Gly
1               5

<210> SEQ ID NO 6
<211> LENGTH: 5
<212> TYPE: PRT
<213> ORGANISM: Flavivirus
<220> FEATURE:
<221> NAME/KEY: MUTAGEN
<222> LOCATION: (1)..(5)
<223> OTHER INFORMATION: Mutation in central monomer contact interface
      of flavivirus envelope protein

<400> SEQUENCE: 6

Gly Asp Gln Thr Lys
1               5

<210> SEQ ID NO 7
<211> LENGTH: 5
<212> TYPE: PRT
<213> ORGANISM: Flavivirus
<220> FEATURE:
<221> NAME/KEY: misc_feature
<223> OTHER INFORMATION: Wild-type central monomer contact interface

<400> SEQUENCE: 7

Gly Ser Gln Glu Gly
1               5

<210> SEQ ID NO 8
<211> LENGTH: 5
<212> TYPE: PRT
<213> ORGANISM: Flavivirus
<220> FEATURE:
<221> NAME/KEY: misc_feature
<223> OTHER INFORMATION: Wild-type central monomer contact interface

<400> SEQUENCE: 8

Gly Asn Gln Glu Gly
1               5

<210> SEQ ID NO 9
<211> LENGTH: 5
<212> TYPE: PRT
<213> ORGANISM: Flavivirus
```

```
<220> FEATURE:
<221> NAME/KEY: misc_feature
<223> OTHER INFORMATION: Wild-type central monomer contact interface

<400> SEQUENCE: 9

Gly Asp Gln Thr Gly
1               5

<210> SEQ ID NO 10
<211> LENGTH: 5
<212> TYPE: PRT
<213> ORGANISM: Flavivirus
<220> FEATURE:
<221> NAME/KEY: misc_feature
<223> OTHER INFORMATION: Wild-type central monomer contact interface

<400> SEQUENCE: 10

Gly Asp Gln Thr Ala
1               5
```

FLAVIVIRUS ENVELOPE PROTEIN MUTATIONS AFFECTING VIRION DISASSEMBLY

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The flavivirus genus incorporates over 60 closely related viruses including several human pathogens of the global and local epidemiological importance. Virions are composed of three structural proteins designated capsid ("C"), membrane ("M"), and envelope ("E"). Immature flavivirions found in infected cells contain pre-membrane ("prM") protein, which is a precursor to the M protein. Immature virions contain prM-E heterodimers composing the virion envelope. The prM protein serves as a chaperone for slowly folding E, prevents E from pH-mediated irreversible rearrangement during transport, and is cleaved prior to virion release. Flavivirus-infected cells release non-infectious subviral particles containing only envelope proteins prM and E. These can be generated by expression of flavivirus prM-E cassettes. Their assembly pathway—intracellular transport, carbohydrate processing, maturation, prM cleavage, and secretion—resembles that of infectious virions.

The E protein comprises a long ectodomain followed by a stem-anchor region. Three-dimensional structures of the flavivirus E protein ectodomain (about 400 amino acids, excluding the carboxy terminal stem and transmembrane domains) and its dimeric and trimeric forms have been solved for E proteins of tick-borne encephalitis and dengue viruses, both in the prefusion and postfusion conformations. See Bressanelli et al., *Structure of a flavivirus envelope glycoprotein in its low-pH-induced membrane fusion conformation*, EMBO J. 12 1-12 (2004); Modis et al., *A ligand-binding pocket in the dengue virus envelope glycoprotein*, Proc Natl Acad Sci USA 100 6986-6991 (2003) Epub May 20, 2003; Modis et al., *Structure of the dengue virus envelope protein after membrane fusion*, Nature 427 313-319 (2004); Modis et al., *Variable surface epitopes in the crystal structure of dengue virus type 3 envelope glycoprotein*, J Virol 79 1223-1231 (2005); and Rey et al., *The envelope glycoprotein from tick-borne encephalitis virus at 2 A resolution*, Nature 375 291-298 (1995), which are incorporated by reference. The ectodomain forms an elongated dimer that is oriented parallel to the viral membrane (see FIG. 1, the top view of a NY99 E400 model derived by homology modeling). In the head-to-tail dimer, each monomer is composed of domains I, II, and III. Monomer contacts in the dimer are not contiguous along the whole length of the molecule. There are two holes along the dimer axis that occupy the place of cleaved prM (see Rey et al., *The envelope glycoprotein from tick-borne encephalitis virus at 2 A resolution*, Nature 375 291-298 (1995)). Beyond two short α-helices in domain II, β-strands are predominant throughout the molecule.

Each of the centrally located N-terminal domains I contains two disulfide bridges and carries a single carbohydrate side chain that shields the fusion peptide located on the tip of domain II and contributes to overall stability of the dimer (see Rey et al., *The envelope glycoprotein from tick-borne encephalitis virus at 2 A resolution*, Nature 375 291-298 (1995)). Domain II, or the dimerization domain, has an elongated finger-like structure and is involved in monomer-to-monomer interaction at two distinct loci. The distal loop is stabilized by three disulfide bridges and forms the tip that holds the fusion peptide, which fits into a hydrophobic pocket provided by domains I and III of the second monomer. This contact is largely nonpolar and is composed of residues from domains I and III on one subunit and the tip of domain II on the other. The contact at the center, where two prominent α-helices can be seen, mostly involves hydrophilic side chains of domain II only. Domain III contains the C terminus and in the virion is connected to the stem followed by the transmembrane region that anchors the monomer in the membrane.

Despite the divergence in amino acid sequences of the E proteins of different flaviviruses, the 12 cysteine residues are absolutely conserved between species. These form six disulfide bridges in the West Nile virus E protein (see Nowak et al., *Analysis of disulfides present in the membrane proteins of the West Nile flavivirus*, Virology 156 127-137 (1987)) and were found at the expected positions in the X-ray structures of all E proteins determined to date. This strongly supports the current understanding that the overall structural organization and folding are similar for E proteins of all flaviviruses.

Exposure to acidic pH leads to dramatic rearrangement of the virion organization accompanied by inactivation of biological activities such as infectivity, membrane binding, and fusion. Induced changes are a crucial component of the fusion process during virus entry. See Corver et al., *Membrane fusion activity of tick-borne encephalitis virus and recombinant subviral particles in a liposomal model system*, Virology 269 37-46 (2000); Heinz et al., *The machinery for flavivirus fusion with host cell membranes*, Curr Opin Microbiol 4 450-455 (2001); and Stiasny et al., *Membrane interactions of the tick-borne encephalitis virus fusion protein E at low pH*, J Virol 76 3784-3790 (2002). The mechanism of pH-induced fusion mediated by the E protein involves rearrangement of E from the dimeric to a trimeric form (see Stiasny et al., *Structural requirements for low-pH-induced rearrangements in the envelope glycoprotein of tick-borne encephalitis virus*, J Virol 70 8142-8147 (1996)). Formation of fusogenic E trimers is a two-step process, in which dimers first dissociate under influence of low pH and then re-associate forming trimers. The two-step model has been first obtained in studies of the E-400 ectodomain. In absence of the stem-anchor region exposure to acidic pH causes reversible dissociation of the dimer that does not lead to trimerization. Further studies demonstrated the functional role of the stem-anchor region (about amino acids 400-449) for the low-pH-induced irreversible conversion of the dimer to the trimer in solution (see Allison et al., *Mapping of functional elements in the stem-anchor region of tick-borne encephalitis virus envelope protein E*, J Virol 73 5605-5612 (1999)). The irreversible change from dimers to trimers induced by low pH suggests that in virions E exists as a metastable dimer and changes to a more stable trimer when the appropriate trigger (in this case low pH) is applied. It was shown that the trimeric form of E is more stable to thermal denaturation than the dimeric form. In contrast to class I fusion proteins, however, such transition to the more stable conformation state cannot be induced by thermal treatment, which only leads to the denaturation of E (see Stiasny et al., *Role of metastability and acidic pH in membrane fusion by tick-borne encephalitis virus*, J Virol 75 7392-7398 (2001)). This suggests that protonation of the native E dimer is indispensable for generating a monomeric intermediate structure that is required for the formation of the energetically more stable final trimeric form (see Heinz et al., *Flavivirus structure and membrane fusion*, Adv Virus Res 59 63-97 (2003)).

For a number of flaviviruses neurovirulent and neuroinvasive phenotypes have been associated with envelope proteins. See Cecilia et al., *Nucleotide changes responsible for loss of neuro invasiveness in Japanese encephalitis virus neutralization-resistant mutants*, Virology 181 70-71 (1991); Chambers et al., *Yellow fever/Japanese encephalitis chimeric viruses: construction and biological properties*, J Virol 73 3095-3101 (1999); Gualano et al., *Identification of a major determinant of mouse neurovirulence of dengue virus type 2 using stably cloned genomic-length cDNA*, J Gen Virol 79 437-446 (1998); Hasegawa et al., *Mutations in the envelope protein of Japanese encephalitis virus affect entry into cultured cells and virulence in mice*, Virology 191 158-165 (1992); Holzmann et al., *A single amino acid substitution in envelope protein E of tick-borne encephalitis virus leads to attenuation in the mouse model*, J Virol 64 5156-5159 (1990); Holzmann et al., *Characterization of monoclonal antibody-escape mutants of tick-borne encephalitis virus with reduced neuro invasiveness in mice*, J Gen Virol 78 31-37 (1997); Jiang et al., *Single amino acid codon changes detected in louping ill virus antibody-resistant mutants with reduced neurovirulence*, J Gen Virol 74 931-935 (1993); McMinn, *The molecular basis of virulence of the encephalitogenic Flaviviruses*, J Gen Virol 78 2711-2722 (1997); Pletnev et al., *Construction and characterization of chimeric tick-borne encephalitis/dengue type 4 viruses*, Proc Natl Acad Sci USA 89 10532-10536 (1992); and Pletnev et al., *Chimeric tick-borne encephalitis and dengue type 4 viruses: effects of mutations on neurovirulence in mice*, J Virol 67 4956-4963 (1993), which are all incorporated by reference. However, mutations in other parts of the genome were also implicated for loss/acquisition of neurovirulence. See Butrapet et al., *Attenuation markers of a candidate dengue type 2 vaccine virus, strain 16681 (PDK-53), are defined by mutations in the 5' noncoding region and nonstructural proteins 1 and 3*, J Virol 74 3011-3019 (2000); Duarte dos Santos et al., *Determinants in the Envelope E Protein and Viral RNA Helicase NS3 That Influence the Induction of Apoptosis in Response to Infection with Dengue Type 1 Virus*, Virology 274 292-308 (2000); Dunster et al., *Molecular and biological changes associated with HeLa cell attenuation of wild-type yellow fever virus*, Virology 261 309-318 (1999); Muylaert et al., *Mutagenesis of the N-linked glycosylation sites of the yellow fever virus NS1 protein: effects on virus replication and mouse neurovirulence*, Virology 222 159-168 (1996); Ni et al., *Molecular basis of attenuation of neurovirulence of wild-type Japanese encephalitis virus strain SA14*, J Gen Virol 76 409-413 (1995); and Xie et al., *Yellow fever 17D vaccine virus isolated from healthy vaccinees accumulates very few mutations*, Virus Res 55 93-99 (1998), which are all incorporated by reference. Attenuation resulting from mutations in protein E is most extensively studied with a live attenuated JE vaccine SA14-14-2, for which 9 amino acid differences have been identified in the E protein that distinguish the attenuated vaccine virus from its virulent parent SA14. The dominant attenuating effect is associated with a E138K mutation located at the so-called "hinge" region interfacing domains I and II (see Rey et al., *The envelope glycoprotein from tick-borne encephalitis virus at 2 A resolution*, Nature 375 291-298 (1995)). The hinge locus is believed to play a crucial role in dimer-to-trimer transition of the E protein associated with virus entry. Modifications within this region modulate virulence of flaviviruses in mice (see Cecilia et al., *Nucleotide changes responsible for loss of neuroinvasiveness in Japanese encephalitis virus neutralization-resistant mutants*, Virology 181 70-71 (1991); Gualano et al., *Identification of a major determinant of mouse neurovirulence of dengue virus type 2 using stably cloned genomic-length cDNA*, J Gen Virol 79 437-446 (1998); Hasegawa et al., *Mutations in the envelope protein of Japanese encephalitis virus affect entry into cultured cells and virulence in mice*, Virology 191 158-165 (1992); Hurrelbrink et al., *Attenuation of Murray Valley encephalitis virus by site-directed mutagenesis of the hinge and putative receptor-binding regions of the envelope protein*, J Virol 75 7692-7702 (2001); McMinn et al., *Murray valley encephalitis virus envelope protein antigenic variants with altered hemagglutination properties and reduced neuroinvasiveness in mice*, Virology 211 10-20 (1995); and Sumiyoshi et al., *Characterization of a highly attenuated Japanese encephalitis virus generated from molecularly cloned cDNA*, J Infect Dis 171 1144-1151 (1995), which are all incorporated by reference). Additional loci important for attenuation or reversion to virulence were defined at positions 176/177 and 264/279 in E and are also present in SA14-14-2. The former is located in the central domain undergoing changes during acid-mediated reorganization of E to fusion competent trimers during virus entry (see Bressanelli et al., *Structure of a flavivirus envelope glycoprotein in its low-pH-induced membrane fusion conformation*, EMBO J. 12 1-12 (2004)). The latter locus is also located in the hinge region and may functionally cooperate with the locus defined by the E138K mutation, since mutations involving nearby positions impair hemagglutination and fusion properties of E and reduce neuroinvasiveness in mice (see Hurrelbrink et al., *Attenuation of Murray Valley encephalitis virus by site-directed mutagenesis of the hinge and putative receptor-binding regions of the envelope protein*, J Virol 75 7692-7702 (2001) and McMinn et al., *Murray valley encephalitis virus envelope protein antigenic variants with altered hemagglutination properties and reduced neuroinvasiveness in mice*, Virology 211 10-20 (1995)). The last cluster of mutations present in SA14-14-2 is located to the domain III and stem-anchor region of the E protein, which are important for virus attachment to cells and for interaction with prM. Mutations around position 315 resulted in altered virus tropism and changes in virulence (see Jennings et al., *Analysis of a yellow fever virus isolated from a fatal case of vaccine-associated human encephalitis*, J Infect Dis 169 512-518 (1994); Jiang et al., *Single amino acid codon changes detected in louping ill virus antibody-resistant mutants with reduced neurovirulence*, J Gen Virol 74 931-935 (1993); Ni et al., *Attenuation of Japanese encephalitis virus by selection of its mouse brain membrane receptor preparation escape variants*, Virology 241 30-36 (1998); and Ryman et al., *Mutation in a 17D-204 vaccine substrain-specific envelope protein epitope alters the pathogenesis of yellow fever virus in mice*, Virology 244 59-65 (1998)). The integrity of the stem-anchor region is also required for stability of the prM-E heterodimer (see Allison et al., *Mapping of functional elements in the stem-anchor region of tick-borne encephalitis virus envelope protein E*, J Virol 73 5605-5612 (1999)). The only amino acid change in SA14-14-2 that is found in the distal monomer contact interface (see FIG. 1) involves a L107F substitution in the highly conserved fusion loop (amino acids 98-110). In the vast majority of flaviviruses, this position is occupied by Leu, with only two known exceptions of the Phe occurrence in Powassan and deer tick flaviviruses that are substantially less virulent American relatives of TBE virus. Reversion of this mutation to Leu was associated with only partial reversion to the neurovirulent phenotype (see Arroyo et al., *Molecular basis for* attenuation of neurovirulence of a yellow fever Virus/Japanese encephalitis virus chimera vaccine (ChimeriVax-JE), J Virol 75 934-942 (2001)) indicating that only minor attenuation changes are tolerated at this locus. Lack of other known mutations at either distal or central contact interfaces indicates the existence of a strong selective pressure against changes influencing dimer formation. This agrees with the importance of this interface both for virion assembly/maturation at the end of the viral infectious cycle and for functional disassembly during the initial phase of the next reproductive cycle.

BRIEF SUMMARY OF THE INVENTION

The present invention is directed to mutations in the central monomer contact interface of the flavivirus envelope protein which modulate the infectivity of the flavivirus. The mutations significantly reduce virus capability to infect host cells resulting in delay or inhibition of virus spread. In contrast to mutations described before, these mutations typically do not affect virus replication or assembly and release of infectious virions from infected cells. Rather, assembled and released virions are inhibited in transition to the pre-fusogenic state characteristic for many, if not all, enveloped viruses as an intermediate state prior to fusion-mediated entry virus into host cells. The resulting virus remain highly immunogenic, yet substantially safer due to its inability to establish productive viremia. The approach opens the possibility of rational design of safe attenuated vaccines that retain immunogenicity similar to the parent pathogen.

Thus, in one aspect, the present invention is directed to one or more mutations in a flavivirus envelope monomer protein capable of forming a dimer along a highly conserved central monomer contact interface. This central monomer contact interface of the flavivirus corresponds to amino acids 256 to 260 of the West Nile virus envelope protein. The envelope protein has one or more mutations in the central monomer contact interface which decrease dissociation of the dimer. In another aspect, the one or more mutations in the flavivirus envelope monomer protein result in at least two salt bridges at the central monomer contact interface. In an exemplary aspect, for mosquito-borne viruses, the amino acid of the flavivirus corresponding to the glycine found at position 256 of the West Nile virus envelope protein is substituted with a basic amino acid, such as lysine or arginine. In another exemplary aspect, for tick borne viruses, the amino acid of the flavivirus corresponding to the glycine found at position 260 of the West Nile virus envelope protein is substituted with a basic amino acid, such as lysine or arginine.

In another aspect, the present invention is directed to a flavivirus envelope monomer protein having a central monomer contact interface comprising a sequence selected from the group consisting of RSQEG (SEQ ID NO: 1), RNQEG (SEQ ID NO: 2), GDQTR (SEQ ID NO: 3), KSQEG (SEQ ID NO: 4), KNQEG (SEQ ID NO: 5), and GDQTK (SEQ ID NO: 6).

In preferred aspects, the flavivirus having the inventive mutations is selected from the group consisting of West Nile virus, Kunjin virus, Japanese encephalitis virus, Murray Valley encephalitis virus, dengue serotype 1 virus, dengue serotype 2 virus, dengue serotype 3 virus, dengue serotype 4 virus, yellow fever virus, tick-borne encephalitis virus, Powassan virus, and Omsk hemorrhagic fever virus.

In another aspect, the present invention is directed poly- nucleotide encoding for the flavivirus envelope monomer protein having the inventive mutations. The present invention is also directed to vectors comprising the polynucleotide, and host cells having such vectors.

In still another aspect, the present invention is directed to a live attenuated flavivirus which encodes the flavivirus envelope dimeric protein having the inventive mutations described herein. In preferred aspects, the flavivirus is selected from the group consisting of West Nile virus, Kunjin virus, Japanese encephalitis virus, Murray Valley encephalitis virus, dengue serotype 1 virus, dengue serotype 2 virus, dengue serotype 3 virus, dengue serotype 4 virus, yellow fever virus, tick-borne encephalitis virus, Powassan virus, and Omsk hemorrhagic fever virus. In yet another aspect, the inventive mutations are in a live chimeric flavivirus. The viruses (whether chimeric or non-chimeric) may also optionally have one or more envelope protein mutations, such as those in amino acid residues corresponding to West Nile virus envelope protein amino acids selected from the group consisting of amino acids 107, 138, 176, 177, 224, 264, 280, 316, and 440.

In still another aspect, the present invention is directed to an immunogenic composition comprising the attenuated flavivirus which encodes the flavivirus envelope dimeric protein having the inventive mutations described herein. Such compositions may be used to administer to patients, including humans. Exemplary routes of administration include intravenous, intramuscular, intraperitoneal, or subcutaneous.

In yet another aspect, the present invention is directed to a recombinant genetic construct for encoding a flavivirus having envelope dimeric proteins with the inventive mutations described herein. The recombinant genetic construct may comprise a vector such as a plasmid. In one aspect, the recombinant genetic construct is infectious DNA encoding an infectious (+) RNA molecule under the control of a eukaryotic promoter. Such recombinant genetic constructs may encode corresponding recombinant proteins. In another aspect, the present invention is directed to a host cell stably or transiently transfected with the recombinant genetic constructs.

In still another aspect, the present invention is directed to an immunogenic composition comprising the recombinant genetic construct which encodes the flavivirus envelope dimeric protein having the inventive mutations described herein. Again, such compositions may be used to administering to patients, including humans. Exemplary routes of administration include intravenous, intramuscular, intraperitoneal, or subcutaneous.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 6 is a model of infectious properties of wt and mutant viruses. BHK cells on glass coverslips were transfected with corresponding infectious DNA, cells fixed at indicated time and stained with WN-specific antiserum followed by anti mouse IgG-FITC conjugate.

FIG. 7 is a chart showing the survival of animals after intracerebral inoculation with 1 µg of modified infectious DNA pCMVNY99.

DETAILED DESCRIPTION OF PREFERRED EMBODIMENT

Figure 1:
FIG. 1 is a three-dimensional model of the NY99 E protein ectodomain. The model was made by homology modeling. The domain boundaries are indicated by ovals and adjacent numerals.

The present invention is directed to the discovery that the flavivirus envelope protein has a highly conserved sequence that provides a central monomer contact interface during dimer formation. Interference with the dimer disassociation is theorized to interfere with viral spread. Thus, the present invention is directed to amino acid modifications in the central monomer contact interface of the flavivirus envelope protein that modulate dimer disassociation. The amino acid modification may include a substitution, insertion, and/or deletion in the polypeptide sequence in the central monomer contact region.

The present invention is directed to a flavivirus envelope monomer protein capable of forming a dimer along a central monomer contact interface at the amino acids of the flavivirus envelope protein corresponding to amino acids 256 to 260 of the West Nile virus envelope protein such that the flavivirus envelope protein has one or more mutations which decrease dissociation of the dimer. In an exemplary embodiment, for mosquito-borne viruses, the amino acid corresponding to position 256 of the West Nile virus envelope protein (i.e., corresponding to G256 of WN) is substituted with a basic amino acid, such as arginine or lysine. The amino acid mutation at position 256 still preferably provides for a symmetrical or near symmetrical interface during the dimer formation. In another exemplary aspect, for tick-borne viruses, the amino acid corresponding to position 260 of the West Nile virus envelope protein (i.e., corresponding to G260 of WN) is substituted with a basic amino acid, such as lysine or arginine. Again, the amino acid mutation at position 260 still preferably provides for a symmetrical or near symmetrical interface during the dimer formation.

The flavivirus may have a wild-type central monomer contact interface comprising a sequence selected from the group consisting of GSQEG (SEQ ID NO: 7), GNQEG (SEQ ID NO: 8), GDQTG (SEQ ID NO: 9), and GDQTA (SEQ ID NO: 10). Thus, in one aspect of the present invention, the central monomer contact interface comprises a Gly to Arg substitution such that the central monomer contact interface has a sequence selected from the group consisting of RSQEG (SEQ ID NO: 1), RNQEG (SEQ ID NO: 2), GDQTR (SEQ ID NO: 3), KSQEG (SEQ ID NO: 4), KNQEG (SEQ ID NO: 5), and GDQTK (SEQ ID NO: 6).

As generally shown in Table 1, nearly all mosquito-borne flaviviruses have the GSQEG (SEQ ID NO: 7) or GNQEG (SEQ ID NO: 8) sequence at the central monomer contact interface. Serine and threonine are both hydroxyl-containing amino acids, aspartic acid and glutamic acid are both negatively charged amino acids, and glycine and alanine are hydrophobic, non-polar amino acids. In West Nile and other mosquito-borne flaviviruses, the amino acid corresponding to G256 in one envelope protein monomer is adjacent to the amino acid corresponding to E259 in the other monomer in models. As a result, the mutations in the amino acid corresponding to a basic amino acid at position G256 described herein lead to formation of two salt bridges ((+) with (−)) such viruses.

As shown in Table 1, nearly all tick-borne flaviviruses have the GDQTG (SEQ ID NO: 9) or GDQTA (SEQ ID NO: 10) sequence at the central monomer contact interface. In tick-borne flaviviruses, the amino acid corresponding to D257 in one envelope protein monomer is adjacent to the amino acid corresponding to G260 (or A260) in the other monomer in models. As a result, the mutations corresponding to a basic amino acid at position G260 described herein lead to formation of two salt bridges ((+) with (−)) in such viruses.

Determination of which amino acid in a given flavivirus corresponds to that of another flavivirus can be carried out by standard amino acid sequence alignment, as is well known to those of skill in this art. Examples of flavivirus sequences which correspond to the West Nile virus are illustrated in Table 1 below. Thus, it will be appreciated that the present invention encompasses mutations at central monomer contact interface which decrease dissociation of the dimer in any flavivirus species or strain.

In one aspect, the flavivirus may be a tick-borne virus, mosquito-borne virus, or a virus without an arthropod vector. The flavivirus may be a mammalian tick-borne virus, such as Alkhurma virus ("ALKV"), Deer tick virus ("DT"), Gadgets Gully virus ("GGYV"), Kadam virus ("KADV"), Karshi virus, Kyasanur Forest disease virus ("KFDV"), Langat virus ("LGTV"), Louping ill virus ("LIV"), Omsk hemorrhagic fever virus ("OHFV"), Powassan virus ("POWV"), Royal Farm virus ("RFV"), tick-borne encephalitis virus ("TBEV"), or Turkish sheep encephalitis virus ("TSE"). The flavivirus may be a seabird tick-borne virus, such as Meaban virus ("MEAV"), Saumarez Reef virus ("SREV"), or Tyuleniy virus ("TYUV"). The flavivirus may be Mosquito-borne viruses, such as Calbertado virus or Duck tembusu virus. The flavivirus may have a no known vertebrate host, such as Aedes flavivirus, Calbertado virus, Cell fusing agent virus, Culex flavivirus, Culex theileri flavivirus, Kamiti River virus, Nakiwogo virus, or Quang Binh virus. The flavivirus may be selected from the group consisting of Aroa virus ("AROAV"), Dengue virus ("DENV"), Kedougou virus ("KEDV"), Bussuquara virus, Cacipacore virus ("CPCV"), Koutango virus ("KOUV"), Ilheus virus ("ILHV"), Japanese encephalitis virus ("JEV"), Murray Valley encephalitis virus ("MVEV"), Rocio virus ("ROCV"), St. Louis encephalitis virus ("SLEV"), Usutu virus ("USUV"), West Nile virus ("WNV"), Yaounde virus ("YAOV"), Kokobera virus ("KOKV"), Bagaza virus ("BAGV"), Ilheus virus ("ILHV"), Israel turkey meningoencephalomyelitis virus ("ITV"), Ntaya virus ("NTAV"), Tembusu virus ("TMUV"), Spondweni virus group, Zika virus ("ZIKV"), Banzi virus ("BANV"), Bouboui virus ("BOUV"), Edge Hill virus ("EHV"), Jugra virus ("JUGV"), Saboya virus ("SABV"), Sepik virus ("SEPV"), Uganda S virus ("UGSV"), Wesselsbron virus ("WESSV"), or Yellow fever virus ("YFV"). Examples of viruses with no known arthropod vector include Entebbe bat virus ("ENTV"), Yokose virus ("YOKV"), Apoi virus ("APOIV"), Cowbone Ridge virus ("CRV"), Jutiapa virus ("JUTV"), Modoc virus ("MODV"), Sal Vieja virus ("SVV"), San Perlita virus ("SPV"), Bukalasa bat virus ("BBV"), Carey Island virus ("CIV"), Dakar bat virus ("DBV"), Montana myotis leukoencephalitis virus ("MMLV"), Phnom Penh bat virus ("PPBV"), and Rio Bravo virus ("RBV"). In one aspect, the flavivirus is selected from the group consisting of West Nile virus, Kunjin virus, Japanese encephalitis virus, Murray Valley encephalitis virus, dengue serotype 1 virus, dengue serotype 2 virus, dengue serotype 3 virus, dengue serotype 4 virus, yellow fever virus, tick-borne encephalitis virus, Powassan virus, and Omsk hemorrhagic fever virus.

In addition to the viruses listed above, chimeric flaviviruses that include the inventive mutations in the central monomer contact interface are within the scope of the invention. In general, a chimeric flavivirus encompasses a virus having a genome containing sequences from two or more different flaviviruses, including different flavivirus strains. For example, these chimeras can comprise of a flavivirus (i.e., a backbone flavivirus) in which a structural protein (or proteins) has been replaced with a corresponding structural protein (or proteins) of a second virus. For example, the chimeras can consist of a backbone flavivirus (e.g., a yellow fever virus) in which the prM and E proteins of the flavivirus have been replaced with the prM and E proteins of the second virus (e.g., a dengue virus (serotypes 1-4), Japanese encephalitis virus, West Nile virus, or another virus, such as any of those mentioned herein). The chimeric viruses can be made from any combination of viruses or strains thereof. Exemplary chimeras are described in Yamshchikov, U.S. Pat. No. 7,455,832 and Guirakhoo et al. U.S. Patent Application No. 2007/0269458, which are incorporated by reference.

The flavivirus envelope proteins of the present invention are useful for preparing attenuated flaviviruses strains. In addition to such use, the proteins are useful as complementary tools to uncover mechanisms of action and functions of the flavivirus envelope proteins. For instance, the proteins may be used for the screening of molecules (able to treat infections induced by a flavivirus) which modulate the activity of the instant proteins. In one aspect, the flavivirus envelope proteins of the present invention may be isolated and/or purified.

In another aspect, the present invention is directed to the nucleotide sequences encoding the proteins as described herein, including all possible examples of nucleotide sequences encoding these proteins which result from the degeneration of the genetic code. Nucleic acids of the invention may be obtained by the well-known methods of recombinant DNA technology and/or chemical DNA synthesis. The invention also provides recombinant constructs comprising a polynucleotide encoding the instant proteins or an attenuated flavivirus strains encoding such proteins. The constructs maybe in the form of a vector in a prokaryotic or eukaryotic host cell transformed by a vector of the invention.

Thus, in another aspect, the present invention is directed also to a live attenuated flavivirus in which the flavivirus envelope monomer protein is capable of forming a dimer along the central monomer contact interface at the amino acids corresponding to amino acids 256 to 260 of the West Nile virus envelope protein, and the flavivirus envelope monomer protein has one or more mutations which decrease dissociation of the dimer.

The live attenuated virus of the present invention may be produced in vivo using an infectious DNA approach, such as that described in Yamshchikov, U.S. Pat. No. 7,459,163 and Yamshchikov, U.S. Pat. No. 7,455,832, which are incorporated by reference. It will be appreciated to those skilled in the art that the infectious DNA of the present invention may be formed using any suitable vector. In general, a vector is a nucleic acid molecule (typically DNA or RNA) that serves to transfer a passenger nucleic acid sequence (i.e., DNA or RNA) into a host cell. Three common types of vectors include plasmids, phages, and viruses. Preferably, the vector is a plasmid. That is, the infectious DNA vaccines of the present invention are comprised of DNA that is produced as a plasmid that can be introduced into animal tissue and therein is expressed by animal cells to produce a messenger ribonucleic acid ("mRNA") molecule of the size of the flavivirus genome, which is translated to produce a viral polyprotein, that is processed by cellular machinery to provide a full set of flavivirus proteins that are capable to initiate replication of the above primary RNA transcript and thus initiate the virus replication cycle in animal tissue into which the above DNA plasmid was introduced.

Suitable and exemplary plasmid vectors that have been used in conventional DNA vaccines include, but are not limited to pBR322 (ATCC#31344); pUC 19 (ATCC#37254); pcDNA3.1 (Invitrogen, Carlsbad, Calif.; Cat. NO. V385-20; DNA sequence available at http://www.invitrogen.com/vectordata/index.html); pNGVL (National Gene Vector Laboratory, University of Michigan, MI); p414cyc (ATCC#87380), p414GALS (ATCC#87344), pBAD18 (ATCC#87393), pBL-CAT5 (ATCC#77412), pBluescriptIIKS, (ATCC#87047), pBSL130 (ATCC#87145), pCM182 (ATCC#87656), pCM-VtkLUC (ATCC#87633), pECV25 (ATCC#77187), pGEM-7zf (ATCC#87048), pGEX-KN (ATCC#77332), pJC20 (ATCC#87113), pUB110 (ATCC#37015), pUB18 (ATCC#37253).

The infectious DNA of the present invention is also preferably under the control of a suitable promoter. For eukaryotic expression, suitable promoters include the cytomegalovirus ("CMV") early promoter, or alternatively the Rous sarcoma virus ("RSV") LTR promoter, and the SV40 promoter.

The amount of the live attenuated virus or recombinant constructs present in the immunogenic compositions of the present invention are preferably a therapeutically effective amount. For example, in the case of a WN recombinant construct, a therapeutically effective amount of plasmid is generally that amount necessary so that the nucleotide sequence coding for the WN virus performs its immunological role without causing overly negative effects in the host to which the composition is administered. The exact amount of plasmid to be used and the composition/vaccine to be administered will vary according to factors such as the strength of the transcriptional promoters used, the type of condition being treated, the mode of administration, as well as the other ingredients in the composition. Preferably, the composition or the vaccine formulation is composed of from about 10 ng to about 1 µg of plasmid. It is important to note that non-replicating DNA vaccines usually require larger amounts of DNA (typically 10 to 100 µg) of plasmid.

The vaccines and pharmaceutical compositions of the present invention can also include pharmaceutically acceptable carriers. Carriers include diluents, adjuvant, excipient, or vehicle with which the attenuated live virus or infectious DNA is administered. Such pharmaceutical carriers can be sterile liquids, such as water and oils, including those of petroleum, animal, vegetable, or synthetic origin, such as peanut oil, soybean oil, mineral oil, sesame oil, and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Carriers may include auxiliary agents including, but not limited to, diluents, stabilizers (i.e., sugars and amino acids), preservatives, wetting agents, emulsifying agents, pH buffering agents, viscosity enhancing additives, colors, and the like. Carriers include, but are not limited to, stabilizers, preservatives, and buffers. Suitable stabilizers are, for example SPGA, Tween compositions (such as are available from A.G. Scientific, Inc., San Diego, Calif.), carbohydrates (such as sorbitol, mannitol, starch, sucrose, dextran, glutamate, or glucose), proteins (such as dried milk serum, albumin, or casein), or degradation products thereof. Non-limiting examples of suitable buffers include alkali metal phosphates. Suitable preservatives are thimerosal, merthiolate, and gentamicin. Diluents include water, aqueous buffer (such as buffered saline), alcohols, and polyols (such as glycerol). The compositions may include alpha-interferon, beta-interferon, gamma-interferon, granulocyte macrophage colony stimulator factor ("GM-CSF"), macrophage colony stimulator factor ("M-CSF"), interleukin 2 ("IL-2"), interleukin 12 ("IL-12"), and/or CpG oligonucleotides. For preparing such compositions, methods well known in the art may be used. The vaccine and immunogenic compositions according to the various embodiments of the present invention can be prepared and/or marketed in the form of a liquid, frozen suspension or in a lyophilized form. Typically, vaccines and/or pharmaceutical compositions prepared according to the present invention contain a pharmaceutically acceptable carrier customarily used for such compositions. Examples of pharmaceutical composition and vaccine formulations are described in Sterner et al., U.S. Pat. No. 8,048,429, which is incorporated by reference.

Subcutaneous injection, intradermal introduction, impression through the skin, and other modes of administration such as intraperitoneal, intravenous, oral, or inhalation delivery are also suitable. For example, vectors containing the infectious DNA of the present invention can be introduced into the desired host by methods known in the art, for example, transfection, electroporation, microinjection, microparticles, microcapsules, transduction, cell fusion, DEAE dextran, calcium phosphate precipitation, lipofection (liposome fusion), use of a gene gun (particle bombardment), or a DNA vector transporter.

Administration may be single or multiple (i.e., single-dose or including a booster). Such administration may be alone or in combination with other active therapeutic agents against flavivirus.

Vaccine purification, other vaccine components, vaccine preparation, and vaccine administration are generally described in Wicker et al. U.S. Published Patent Application No. 2009/0117149 and Brown et al. U.S. Published Patent Application No. 2011/0236421, which are all incorporated by reference.

The present invention also relates to a recombinant construct and pharmaceutical composition for eliciting an immune response or a protective immunity against pathogenic flavivirus strains, including the highly pathogenic NY99 virus strain. According to a related aspect, the present invention relates to a vaccine for preventing and/or treating a flavivirus-associated disease.

The terms "a" or "an" may mean one or more. As used herein in the claim(s), when used in conjunction with the word "comprising," the words "a" or "an" may mean one or more than one.

The term "about" is used to indicate that a value includes the inherent variation of error for the device, the method being employed to determine the value, or the variation that exists among the study subjects.

The terms "encode" or "encoding" with reference to a nucleic acid are used to make the invention readily understandable by the skilled artisan; however, these terms may be used interchangeably with "comprise" or "comprising" respectively.

The use of the term "or" used to mean "and/or" unless explicitly indicated to refer to alternatives only or the alternatives are mutually exclusive, although the disclosure supports a definition that refers to only alternatives and "and/or." As used herein "another" may mean at least a second or more.

The terms "peptide," "oligopeptide," "polypeptide," "polyprotein," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "treating" refers to a process by which the symptoms of flavivirus viral replication or associated disease are inhibited, ameliorated, or completely eliminated. As used herein, the term "preventing" refers to a process by which a flavivirus viral replication or associated disease is obstructed or delayed.

The term "recombinant," as used herein, means that a particular sequence is the product of various combinations of cloning, restriction, and/or ligation steps resulting in a construct having a structural coding sequence distinguishable from homologous sequences found in natural systems. For example, DNA sequences encoding the structural coding sequence can be assembled from cDNA fragments and short oligonucleotide linkers, or from a series of oligonucleotides, to provide a synthetic gene that is capable of being expressed in a recombinant transcriptional unit. Such sequences can be provided in the form of an open reading frame uninterrupted by internal nontranslated sequences, or introns, which are typically present in eukaryotic genes. Conversely, for stabilization purposes such sequences can be provided in the form of an open reading frame interrupted by insertion of artificial non-translated sequences, or introns, which naturally are not present in viral genes. Genomic DNA comprising the relevant sequences could also be used. Sequences of non-translated DNA, other than introns, may also be present 5' or 3' from the open reading frame, where such sequences do not interfere with manipulation or expression of the coding regions. Thus, for example, the term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

The term "construct" generally refers to recombinant nucleic acid, generally recombinant DNA, that has been generated for the purpose of the expression of a specific nucleotide sequence(s), or is to be used in the construction of other recombinant nucleotide sequences.

Similarly, the terms "recombinant protein" refers to a polypeptide or polyprotein that is not naturally occurring, or is made by the artificial combination of two otherwise separated segments of amino acid sequences. This artificial combination may be accomplished by standard techniques of recombinant DNA technology, such as described above, i.e., a recombinant protein may be encoded by a recombinant polynucleotide. Thus, a recombinant protein is an amino acid sequence encoded by all or a portion of a recombinant polynucleotide.

The term "immunologically active" or "immunogenic" refers to the capability of the natural, recombinant, or synthetic virus or peptide, or the natural, recombinant, or synthetic nucleic acids encoding such virus or peptide, to induce a specific humoral and/or cellular immune response upon inoculation in the patient.

Thus, the term "immune response" refers to a T-cell response or increased serum levels of antibodies to an antigen, or to the presence of neutralizing antibodies to an antigen, such as a flavivirus protein.

The term "protection" or "protective immunity" refers herein to the ability of the serum antibodies or T-cell response induced during immunization to protect (partially or totally) against disease or death caused by the flavivirus.

The term "subject" or "patient" of the present invention is preferably a bird, e.g., such as chickens, crows, hawks, parrots, geese, flamingos, etc., or mammal, e.g., such as mice, cows, pigs, horses, chickens, cats, dogs, etc., and is preferably a human.

The term "therapeutically effective dose" or "therapeutically effective amount" means a dose or amount that produces the desired effect for which it is administered. The exact dose will depend on the purpose of the treatment, and will be ascertainable by one skilled in the art using known techniques.

The term "pharmaceutically acceptable" means approved by a regulatory agency of the federal or a state government or listed in the U.S. Pharmacopeia or other generally recognized pharmacopeia for use in animals, and more particularly, in humans. Thus, as used herein, the term "pharmaceutically acceptable carrier" means, but is not limited to, a vehicle for containing the DNA constructs or the attenuated live virus of the present invention that can be inoculated into a mammalian host without adverse effects.

Although the present invention has been described to mutation in the central monomer contact interface, it will be appreciated that the viruses of the invention can also include one or more additional mutations. For example, in the case of West Nile virus (or other flaviviruses), such an additional mutation(s) can be in the region of position 107 (e.g., L to F), 316 (e.g., A to V), or 440 (e.g., K to R) (or a combination thereof) of the West Nile virus envelope protein. The mutations can thus be, for example, in one or more of amino acids 102-112, 138 (e.g., E to K), 176 (e.g., Y to V), 177 (e.g., T to A), 244 (e.g., E to G), 264 (e.g., Q to H), 280 (e.g., K to M), 311-321, and/or 435-445 of the West Nile envelope protein. As a specific example, using the sequence of West Nile virus strain NY99-flamingo 382-99 (GenBank Accession Number AF196835) as a reference, the lysine at position 107 can be replaced with phenylalanine, the alanine at position 316 can be replaced with valine, and/or the lysine at position 440 can be replaced with arginine. Examples of additional combinations of amino acids that can be mutated include are as follows: 176, 177, and 280; 176, 177, 244, 264, and 280; and 138, 176, 177, and 280. Further, these mutations can also be present in corresponding amino acids of other Flaviviruses, as described herein.

The following examples are included to demonstrate exemplary embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 2:
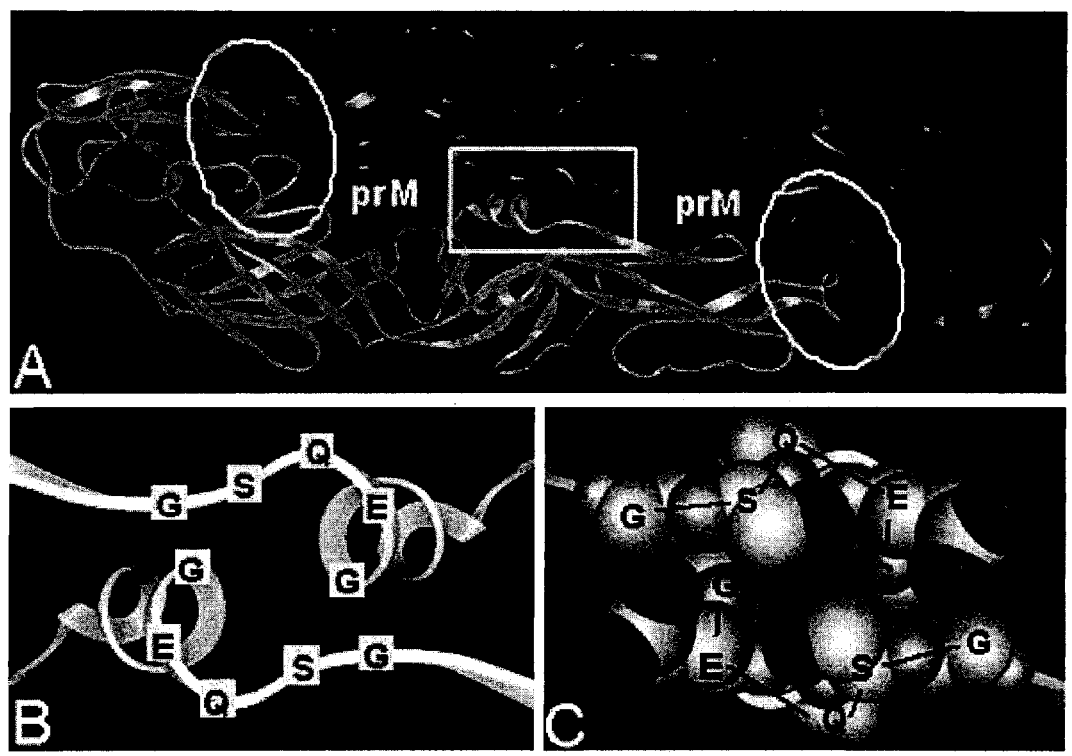
FIG. 2 is a three-dimensional model of the pre-fusion dimeric form of the NY99 E protein ectodomain. Panel A is the top view of the dimer with the protein backbone shown as solid ribbons. Panels B and C show expanded views of the central contact interface shown in panel A. The N→C direction of the upper chain is from the front upper left to back in the upper right; the N→C direction of the lower chain is from the front in the lower right to the back in the lower left. The amino acids at the contact interface are shown schematically (panel B) or in a space fill representation (panel C). For clarity, the sequence outline in the latter does not exactly follow the polypeptide backbone. That is, the positioning of the amino acid letters does not follow the polypeptide backbone, which is traced by connected -αC—N-αC—N-αC— atoms of adjacent amino acids, since not all of the amino acids in the backbone are clearly visible in space fill representation.

Homology Modeling of the WN NY99 Envelope Protein and Analysis of the Monomer Contact Interface The coordinate files of DEN2 (PDB #1OAN, (see Modis et al., *A ligand-binding pocket in the dengue virus envelope glycoprotein*, Proc Natl Acad Sci USA 100 6986-6991 [Epub May 20, 2003] (2003)) and DEN3 (PDB #1UZG, (see Modis et al., *Variable surface epitopes in the crystal structure of dengue virus type 3 envelope glycoprotein*, J Virol 79 1223-1231 (2005)) E homodimers were used in homology modeling with Swiss Model (see Guex et al., *SWISS-MODEL and the Swiss-PdbViewer: an environment for comparative protein modeling*, Electrophoresis 18 2714-2723 (1997) and Schwede et al., *SWISS-MODEL: an automated protein homology-modeling server*, Nucl Acids Res 31 3381-3385 (2003)) to build a model of the NY99 ectodomain dimer; the models were displayed, explored, and manipulated with 3D Molecule Viewer from Vector NTI software package (Invitrogen). As shown in FIG. 2, the contact interface between two monomers is not contiguous with two holes in place of prM (see Rey et al., *The envelope glycoprotein from tick-borne encephalitis virus at 2 A resolution [see comments]*, Nature 375 291-298 (1995)). Areas of close contacts are formed in the center of the dimer and symmetrically at its either distal parts, marked on FIG. 2A by a box and two ovals, respectively. The distal contacts involve largely nonpolar amino acids with the cd fusion loop fitted into a hydrophobic pocket formed by domains I and III.

Figure 3:
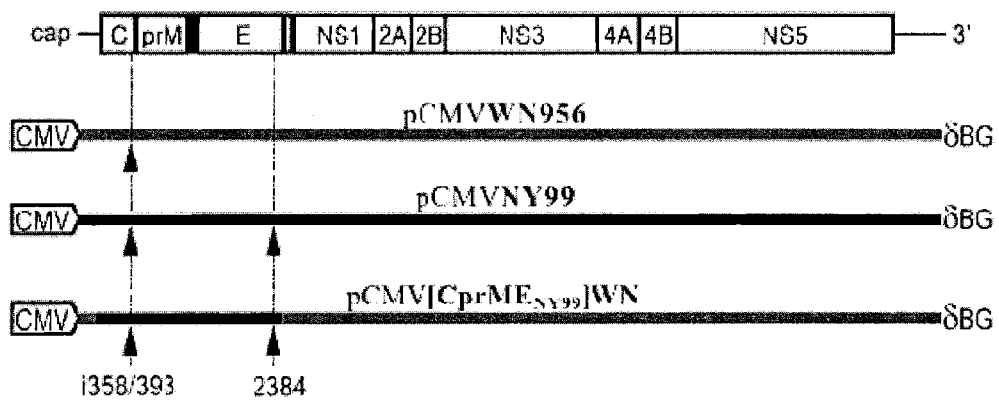
FIG. 3 is a schematic of the infections DNA construct used in the present invention. δ—hepatitis δ ribozyme sequence; BG—bovine growth hormone transcription termination and polyadenylation signal sequence; CMV—cytomegalovirus promoter/enhancer sequence; bla—ampicillin resistance gene; ori—pBR322 replication origin; i2383 and i358/393 marks position of intron. Individual elements are not drawn to scale.
Figure 4:
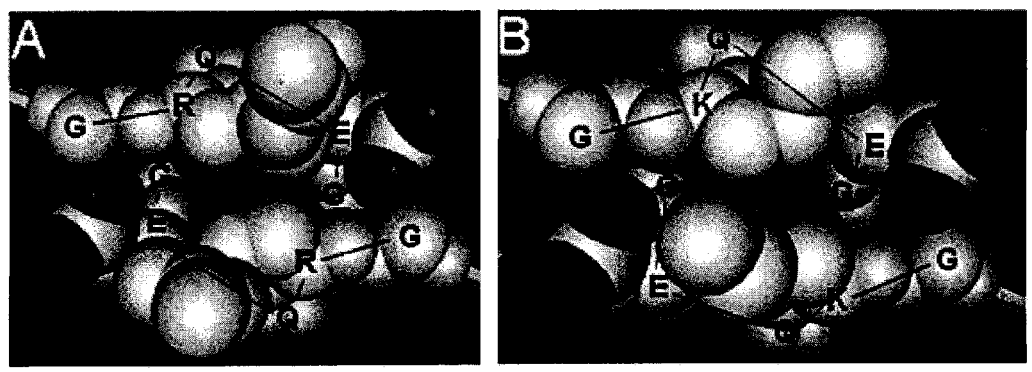
FIG. 4 is a three-dimensional model of the pre-fusion dimeric form of the NY99 E protein ectodomain with a Ser257Arg (panel A) and Ser257Lys (panel B) mutation. Homology modeling was performed using SwissModel and coordinate files PDB #1OAN and PDB #1UZG.

In contrast, the central contact interface, shown in detail in FIGS. 2B and 2C, includes mostly hydrophilic and polar amino acids. The amino acids that compose the two identical α-helices provided by each chain do not seem to form close contacts. The polypeptide chains of two monomers cross at a sharp angle at this locus in the dimer, resembling "X" (if viewed from the side corresponding to the upper part of the picture plane), with the helices occupying the upper left and right corners of the "X" arrangement. However, amino acids surrounding the intersection (GSQEG, shown schematically in FIG. 2B and as space fill in FIG. 2C) do seem to form a close contact. As shown in Table 1, the sequence in fact is highly conserved not only among strains of the same species, but also among members of the genus. Notably, the entire subgroup of tick-borne viruses carries a reciprocal exchange (S→D and E→T) at positions 257 and 259, thus maintaining a combination of negatively charged and hydroxyl-containing amino acids at these positions. On the space fill representation of this sequence (FIG. 2C), the hydroxyl side chains of Ser-257 in each strand are juxtaposed. The hydroxyl groups are equally close (3.11 vs 3.15 Å) to backbone NH of either Gln-258 or Glu-259 of the same chain, and likely form hydrogen bonds. The oxygen atoms of the Glu-259 side chain in one strand are close (3.06-3.14 Å) to backbone NH of Ser-257 in the opposing strand to form a hydrogen bond that may contribute to the stability of dimer. The side chains of conserved Gln-258 are exposed in both strands on the back side of the picture plane in FIG. 2C and do not seem to be in a close proximity to other elements of the structure. Selective pressure for small amino acids (Gly or Ala) at positions 256 and 260 may be imposed by space constraints of the highly symmetrical arrangement at the contact interface.

and stabilize the infectious clone, it was converted to the infectious DNA (iDNA) format using the scheme developed for stabilization of JE infectious DNA (see Yamshchikov et al., *A new strategy in design of +RNA virus infectious clones enabling their stable propagation in E. coli*, Virology 281 272-280 (2001)). The SP6 promoter in the pSP6WN956 construct was replaced with the CMV promoter and a 132 bp artificial intron was inserted at position 358 (at the end of the capsid gene) to increase the stability of the construct during propagation in *E. coli*. An antisense strand hepatitis δ ribozyme followed by the bovine growth hormone transcription termination signal ("BG") was engineered to the end of WN cDNA for an increased fidelity of 3'-end formation, giving rise to the final construct pCMVWN956(i358)δBG (further referred to as pCMVWN956; FIG. 3). Virus amplification foci are easily detectable by indirect immunofluorescence 24 hours after transfection with this plasmid (FIG. 4). The specific infectivity of WN iDNA is 1-5×10$^6$ pfu/µg DNA in Vero cells.

Isolate 385-99 was provided by R. Tesh (Galveston, Tex.) at Vero passage 1. The virus had been recovered from a snowy owl that died in Bronx Zoo, NYC in August 1999. Due to the geographic location and timing of the isolation, it very likely represents an independent isolate of the NY99 strain. The complete nucleotide sequence of the 385-99 genome (GenBank #DQ211652) determined at Vero passage 2 differs from the nucleotide sequence of the same isolate submitted earlier (GenBank #AY842931) in one silent A→G substitution at position 630. The 385-99 isolate differs in 8 nucleotides from

TABLE 1

Alignment of Amino Acid sequences at the central monomer contact interface corresponding to positions 256 to 260 of the West Nile Virus

| Abbr. | Name | | | 256 * | | | | 260 * | | |
|---|---|---|---|---|---|---|---|---|---|---|
| WN NY99 | West Nile virus | I | A | L | G | S | Q | E | G | A | L |
| KUN | Kunjin virus | | | | | | | | | | |
| JEV | Japanese encephalitis virus | V | . | . | . | . | . | . | . | G | . |
| MVE | Murray Valley encephalitis virus | V | . | . | . | . | . | . | . | . | . |
| DEN1 | Dengue virus type 1 | V | V | . | . | . | . | . | . | . | M |
| DEN2 | Dengue virus type 2 | V | V | . | . | . | . | . | . | . | M |
| DEN3 | Dengue virus type 3 | V | V | . | . | . | . | . | . | . | M |
| DEN4 | Dengue virus type 4 | T | V | . | . | . | . | . | . | . | M |
| YFV | Yellow fever virus | L | . | . | . | N | . | . | . | S | . |
| TBE | Tick-borne encephalitis virus | Y | N | . | . | D | . | T | . | V | . |
| POW | Powassan virus | F | N | . | . | D | . | T | A | V | . |
| OHF | Omsk hemorrhagic fever virus | Y | N | . | . | D | . | T | . | V | . |
| ALKV | Alkhumra virus | F | N | . | . | D | . | T | . | I | . |
| DT | Deer tick virus | F | N | . | . | D | . | T | A | V | . |
| LGTV | Langat virus | F | N | . | . | D | . | T | . | V | . |
| LIV | Louping Ill virus | Y | N | . | . | D | . | T | . | V | . |
| SREV | Saumarez Reef virus | H | S | . | . | D | . | T | . | . | V |
| TYUV | Tyuleniy virus | Y | . | . | . | D. | . | T | . | T | V |
| SLE | St. Louis encephalitis virus | V | . | . | . | . | . | . | . | . | . |
| USUV | Usutu virus | V | . | . | . | . | . | . | . | . | . |

For clarity, the two amino acids flanking both sides of the central monomer contact interface are also provided in Table 1.

Example 2

Infectious Clones of WN Flaviviruses

The assembly of a stable infectious clone of WN lineage 2 virus (pSP6WN956) has been reported. See Yamshchikov et al., *An infectious clone of the West Nile flavivirus*, Virology 281 294-304 (2001). This clone was assembled under transcriptional control of the SP6 promoter. To simplify handling the prototype NY99 isolate 382-99 (GenBank #AF196835), and in one amino acid at E167 (Phe→Leu). In contrast to pSP6WN956, a similar pSP6NY99 construct was very unstable and displayed a high tendency to spontaneous rearrangements. The iDNA format allows stabilization of such unstable constructs by insertion of short introns preventing expression of problem regions during propagation in *E. coli* (see Mishin et al., *A 'minimal' approach in design of flavivirus infectious DNA*, Virus Res 81 113-123 (2001) and Yamshchikov et al., *A new strategy in design of +RNA virus infectious clones enabling their stable propagation in E. coli*, Virology 281 272-280 (2001)); introns are precisely removed by the eukaryotic transcription machinery after transfection of susceptible cells restoring the viral ORF. Insertion of introns at positions 393 and 2384 permitted assembly of a relatively stable NY99 infectious clone. The pCMVNY99 (i393i2384)δBG construct (further referred to as pCMVNY99, FIG. 3) yields antigen-positive foci at 24 hours post-transfection and an almost completely infected monolayer 40 hours post-transfection. The specific infectivity is $5-8 \times 10^6$ pfu/µg; virus recovered from this iDNA has the same biological properties as parent 385-99 (results not shown). The above two iDNA plasmids were used to create chimeric constructs carrying reciprocal exchanges of structural protein genes. One of such chimera pCMV[CprME$_{NY99}$]WN956, a derivative of which is used by the inventor in the ongoing development of human attenuated West Nile vaccine, is shown in FIG. 3. It carries all structural proteins of 385-99 in place of those of WN956 and combines the high immunogenicity of the former with the attenuated phenotype of the latter.

Example 3

Identification of Mutations Affecting Virus Infectivity

As described above, the highly conserved sequence GSQEG forms the essentially palindromic central monomer contact interface in the E dimer. In modeling experiments, a few mutations were selected that may strengthen interaction at this contact interface and affect the vital for virus infectivity pH-mediated disassembly of dimers.

The rationale: selecting mutations that may strengthen monomer-to-monomer interaction. The palindromic nature of the central contract interface originates from the two-fold symmetry of the dimer, which can be seen in the top view in FIG. 2A. The expanded view in FIGS. 2B and 2C shows that in the wild type protein the GSQEG sequence forms a highly symmetrical contact. Preservation of this symmetry was included as an important factor in our mutation modeling experiments. In other words, amino acids that could not adopt a side chain conformation to yield a symmetrical or nearly symmetrical interface were rejected. In general, mutations that would interfere with monomer-to-monomer interaction at this interface were not investigated. It is reasonable to expect that such mutations are detrimental for virion assembly. In contrast, mutations that strengthen interaction between monomers may have a negligible impact on virion assembly, but rather adversely affect dissociation of the dimer. The symmetry of the interface implies that a single mutation in the GSQEG sequence will result in a double effect at the interface due to contribution of each chain.

The presence of a highly conserved negatively charged amino acid (E for mosquito-borne flaviviruses and D for the tick-borne subgroup) prompted investigation about whether the monomer interaction at the contact interface could be strengthened by introduction of a positively charged amino acid that could form a salt bridge with it. As mentioned above, Gln-258 side chains are exposed on the back side of the FIG. 2C picture plane their potential interaction partners were not identified. However, both Gly-256 and Ser-257 in one strand appear in a close proximity to the side chain of Glu-259 in the other strand, prompting exploration of the mutations at these locations. Modeling of E mutant proteins with Ser-257 replaced by Arg or Lys is shown in FIGS. 4A and 4B. It is evident that neither Arg-257 or Lys-257 could form a symmetrical interface. Attempts to improve the symmetry of side chain folding at both strands by manipulating torsion angles (using SwissProt DeepView 3.7) were not successful due to multiple clashes between atoms (results not shown). Although Arg-257 could fit slightly better, the resulting arrangement indicates that the Arg-257 side chain in either strand appears in a proximity to the Glu-259 side chain of the same strand. Thus, the desired potential salt bridge between two strands could not be formed.

Figure 5:
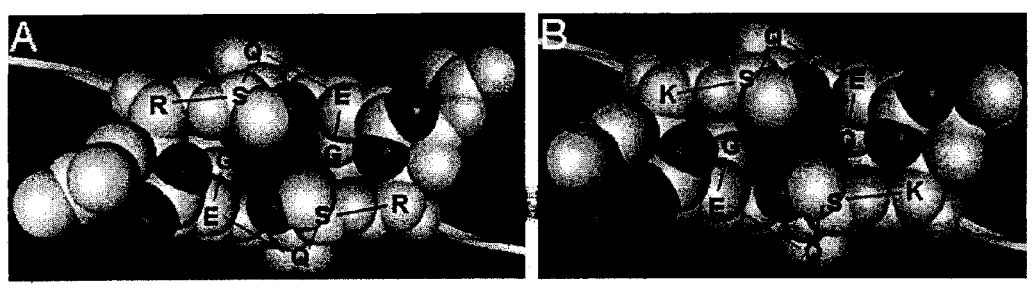
FIG. 5 is a three-dimensional model of the pre-fusion dimeric form of the NY99 E protein ectodomain with a Gly256Arg (panel A) and Gly256Lys (panel B) mutation. Homology modeling was performed using SwissModel and coordinate files PDB #1OAN and PDB #1UZG.

Modeling of E mutant proteins with Gly-256 replaced by Arg or Lys produced more encouraging results. Both resulting RSQEG (FIG. 5A) and KSQEG (FIG. 5B) appear to form nearly symmetrical interfaces and manipulation of torsion angles produced a few rotamers with improved symmetries without clashes between atoms (results not shown). Most importantly, the side chains of both Arg-256 and Lys-256 in one strand appear in a close proximity to the Glu-259 side chain of the other strand and thus could form the desired salt bridges between strands. As mentioned above, a single mutation would result in formation of two salt bridges at either side of the palindromic contact interface. For this reason, the Gly256Arg and Gly256Lys mutations were selected to explore their effects on formation and behavior of the NY99 E protein dimer and on the biological properties of NY99 virus.

Example 4

Design of Mutant Constructs Recovery and Biological Properties of Mutant Viruses To examine the attenuating effect of described modification, Gly256Arg and Gly256Lys mutations into pCMVNY99 infectious DNA construct were introduced as shown in FIG. 3. For comparison, the sequence GSQEG (found in mosquito-borne viruses) was changed to GDQTG for that characteristic for tick-borne flaviviruses. The pCMVNY99 plasmid normally produces highly infectious and highly virulent NY99 virus both upon transfection of mammalian cells and after direct inoculation of mice. The latter results in 100% mortality of animals after inoculation of as little as 1 pg of infectious DNA by any route (i.m., i.d., i.c.).

Figures 6, 7:
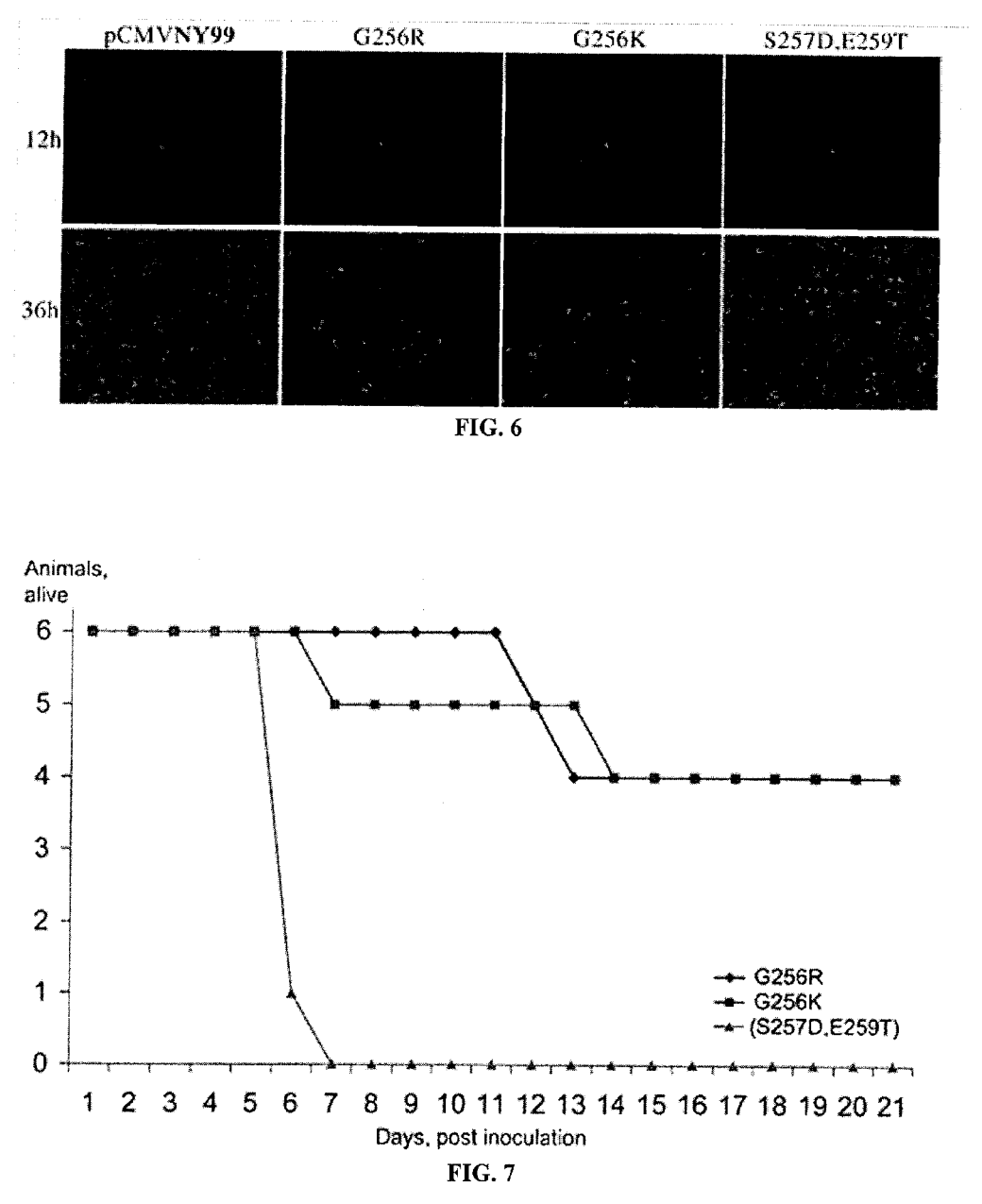

As shown in FIG. 6, both dimer-strengthening mutations had pronounced effect on virus infectivity resulting in delay of virus spread in transfected mammalian cells, as compared to NY99 virus produced from the wild-type construct. In contrast, insertion of the tick-borne flavivirus configurations had no obvious effect on virus infectivity.

Virulence of mutant derivatives was tested in the adult mouse intracerebral inoculation model. Groups of six 5-6 week old mice were inoculated i.c. with 1 µg of the G256R, G256K, or (S257D,E259T) derivatives of pCMVNY99, and animals were observed for 21 days for mortality. Moribund animals were euthanized and counted as they succumbed to infection, which was confirmed by virus presence in brain by virus-specific RT-PCR. In agreement with transfection experiments, the (S257D,E259T) mutant was highly virulent killing all animals on day 5 post inoculation. In contrast, only two mice in each of the G256R, G256K groups were found morbid and were euthanized; however, demonstration of the virus presence in brains by RT-PCR was not made. Assuming nevertheless that animal death was caused by infection, the 67% survival rate in such a stringent test as intracerebral inoculation indicates a high attenuation level of both mutant viruses. All survived animals demonstrated high levels of NY99-specific antibodies with end-point dilution titers exceeding 1:2560, indicating that the animals indeed were exposed to infectious DNA.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The following references, to the extent that they provide exemplary procedural or other details supplementary to those set forth herein, are specifically incorporated herein by reference.

Allison et al., *Synthesis and secretion of recombinant tick-borne encephalitis virus protein E in soluble and particulate form*, J Virol 69 5816-5820 (1995).

Allison et al., *Mapping of functional elements in the stem-anchor region of tick-borne encephalitis virus envelope protein E*, J Virol 73 5605-512 (1999).

Arroyo et al., *Molecular basis for attenuation of neurovirulence of a yellow fever Virus/Japanese encephalitis virus chimera vaccine (ChimeriVax-JE)*, J Virol 75 934-942 (2001).

Bressanelli et al., *Structure of a flavivirus envelope glycoprotein in its low-pH-induced membrane fusion conformation*, EMBO J. 12 1-12 (2004).

Butrapet et al., *Attenuation markers of a candidate dengue type 2 vaccine virus, strain 16681 (PDK-53), are defined by mutations in the 5′ noncoding region and nonstructural proteins 1 and 3*, J Virol 74 3011-3019 (2000).

Cecilia et al., *Nucleotide changes responsible for loss of neuroinvasiveness in Japanese encephalitis virus neutralization-resistant mutants*, Virology 181 70-77 (1991).

Chambers et al., *Yellow fever/Japanese encephalitis chimeric viruses: construction and biological properties*, J Virol 73 3095-3101 (1999).

Chang et al., *Enhancing biosynthesis and secretion of pre-membrane and envelope proteins by the chimeric plasmid of dengue virus type 2 and Japanese encephalitis virus*, Virology 306 170-180 (2003).

Corver et al., *Membrane fusion activity of tick-borne encephalitis virus and recombinant subviral particles in a liposomal model system*, Virology 269 37-46 (2000).

Davis et al., *West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays*, J Virol 75 4040-4047 (2001).

Duarte dos Santos et al., *Determinants in the Envelope E Protein and Viral RNA Helicase NS3 That Influence the Induction of Apoptosis in Response to Infection with Dengue Type 1 Virus*, Virology 274 292-308 (2000).

Dunster et al., *Molecular and biological changes associated with HeLa cell attenuation of wild-type yellow fever virus*, Virology 261 309-318 (1999).

Gualano et al., *Identification of a major determinant of mouse neurovirulence of dengue virus type 2 using stably cloned genomic-length cDNA*, J Gen Virol 79 437-446 (1998).

Guex et al., *SWISS-MODEL and the Swiss-PdbViewer: an environment for comparative protein modeling*, Electrophoresis 18 2714-2723 (1997).

Hasegawa et al., *Mutations in the envelope protein of Japanese encephalitis virus affect entry into cultured cells and virulence in mice*, Virology 191 158-165 (1992).

Heinz et al., *Flavivirus structure and membrane fusion*, Adv Virus Res 59 63-97 (2003).

Heinz et al., *The machinery for flavivirus fusion with host cell membranes*, Curr Opin Microbiol 4 450-455 (2001).

Holzmann et al., *A single amino acid substitution in envelope protein E of tick-borne encephalitis virus leads to attenuation in the mouse model*, J Virol 64 5156-5159 (1990).

Holzmann et al., *Characterization of monoclonal antibody-escape mutants of tick-borne encephalitis virus with reduced neuroinvasiveness in mice*, J Gen Virol 78 31-37 (1997).

Hunt et al., *A recombinant particulate antigen of Japanese encephalitis virus produced in stably-transformed cells is an effective noninfectious antigen and subunit immunogen*, J Virol Methods 97 133-149 (2001).

Hurrelbrink et al., *Attenuation of Murray Valley encephalitis virus by site-directed mutagenesis of the hinge and putative receptor-binding regions of the envelope protein*, J Virol 75 7692-7702 (2001).

Jennings et al., *Analysis of a yellow fever virus isolated from a fatal case of vaccine-associated human encephalitis*, J Infect Dis 169 512-518 (1994).

Jiang et al., *Single amino acid codon changes detected in louping ill virus antibody-resistant mutants with reduced neurovirulence*, J Gen Virol 74 931-935 (1993).

Lorenz et al., *Folding and dimerization of tick-borne encephalitis virus envelope proteins prM and E in the endoplasmic reticulum*, J Virol 76 5480-5491 (2002).

Mason et al., *Japanese encephalitis virus-vaccinia recombinants produce particulate forms of the structural membrane proteins and induce high levels of protection against lethal JEV infection*, Virology 180 294-305 (1991).

McMinn, *The molecular basis of virulence of the encephalitogenic flaviviruses*, J Gen Virol 78 2711-2722 (1997).

McMinn et al., *Murray valley encephalitis virus envelope protein antigenic variants with altered hemagglutination properties and reduced neuroinvasiveness in mice*, Virology 211 10-20 (1995).

Mishin et al., *A 'minimal' approach in design of flavivirus infectious DNA*, Virus Res 81 113-123 (2001).

Modis et al., *A ligand-binding pocket in the dengue virus envelope glycoprotein*, Proc Natl Acad Sci USA 100 6986-6991 [Epub May 20, 2003] (2003).

Modis et al., *Structure of the dengue virus envelope protein after membrane fusion*, Nature 427 313-319 (2004).

Modis et al., *Variable surface epitopes in the crystal structure of dengue virus type 3 envelope glycoprotein*, J Virol 79 1223-1231 (2005).

Muylaert et al., *Mutagenesis of the N-linked glycosylation sites of the yellow fever virus NS1 protein: effects on virus replication and mouse neurovirulence*, Virology 222 159-168 (1996).

Ni et al., *Attenuation of Japanese encephalitis virus by selection of its mouse brain membrane receptor preparation escape variants*, Virology 241 30-36 (1998).

Ni et al., *Molecular basis of attenuation of neurovirulence of wild-type Japanese encephalitis virus strain SA14*, J Gen Virol 76 409-413 (1995).

Nowak et al., *Analysis of disulfides present in the membrane proteins of the West Nile flavivirus*, Virology 156 127-137 (1987).

Pletnev et al., *Construction and characterization of chimeric tick-borne encephalitis/dengue type 4 viruses*, Proc Natl Acad Sci USA 89 10532-10536 (1992).

Pletnev et al., *Chimeric tick-borne encephalitis and dengue type 4 viruses: effects of mutations on neurovirulence in mice*, J Virol 67 4956-4963 (1993).

Rey et al., *The envelope glycoprotein from tick-borne encephalitis virus at 2 A resolution [see comments]*, Nature 375 291-298 (1995).

Ryman et al., *Mutation in a 17D-204 vaccine substrain-specific envelope protein epitope alters the pathogenesis of yellow fever virus in mice*, Virology 244 59-65 (1998).

Schwede et al., *SWISS-MODEL: an automated protein homology-modeling server*, Nucl Acids Res 31 3381-3385 (2003).

Stiasny et al., *Role of metastability and acidic pH in membrane fusion by tick-borne encephalitis virus*, J Virol 75 7392-7398 (2001).

Stiasny et al., *Structural requirements for low-pH-induced rearrangements in the envelope glycoprotein of tick-borne encephalitis virus*, J Virol 70 8142-8147 (1996).

Stiasny et al., *Membrane interactions of the tick-borne encephalitis virus fusion protein Eat low pH*, J Virol 76 3784-3790 (2002).

Sumiyoshi et al., *Characterization of a highly attenuated Japanese encephalitis virus generated from molecularly cloned cDNA*, J Infect Dis 171 1144-1151 (1995).

Xie et al., *Yellow fever 17D vaccine virus isolated from healthy vaccinees accumulates very few mutations*, Virus Res 55 93-99 (1998).

Yamshchikov et al., *The suitability of yellow fever and Japanese encephalitis vaccines for immunization against West Nile virus*, Vaccine 23 4785-4792 (2005).

Yamshchikov et al., *An attenuated West Nile prototype virus is highly immunogenic and protects against the deadly NY99 strain: a candidate for live WN vaccine development*, Virology 330 304-312 (2004).

Yamshchikov et al., *A new strategy in design of +RNA virus infectious clones enabling their stable propagation in E. coli*, Virology 281 272-280 (2001).

Yamshchikov et al., *Regulation of the late events in flavivirus protein processing and maturation*, Virology 192 38-51 (1993).

Yamshchikov et al., *An infectious clone of the West Nile flavivirus*, Virology 281 294-304 (2001).

---

What is claimed and desired to be secured by Letters Patent is as follows:

1. A flavivirus envelope monomer protein capable of forming a dimer along a central monomer contact interface, said flavivirus envelope protein having a central monomer contact interface sequence corresponding to amino acids 256 to 260 of the West Nile virus envelope protein, and wherein said flavivirus envelope protein has a mutation in the central monomer contact interface sequence relative to a wild type sequence selected from the group consisting of GSQEG (SEQ ID NO: 7), GNQEG (SEQ ID NO: 8), GDQTG (SEQ ID NO: 9), and GDQTA (SEQ ID NO: 10), wherein the mutation does not result in a sequence of RSQEG (SEQ ID NO: 1), and wherein said mutation results in formation of two salt bridges at the central monomer contact interface, which decreases dissociation of the dimer relative to the wild type sequence.

2. The protein of claim 1 wherein said flavivirus envelope monomer protein is from a mosquito-borne virus, and wherein said mutation comprises a mutation in which the amino acid of the flavivirus envelope monomer protein corresponding to amino acid 256 of the West Nile virus envelope protein is substituted with a basic amino acid.

3. The protein of claim 2 wherein said basic amino acid is selected from the group consisting of lysine and arginine.

4. The protein of claim 1 wherein said flavivirus envelope monomer protein is from a tick-borne virus, and wherein said mutation comprises a mutation in which the amino acid corresponding to amino acid 260 of the West Nile virus envelope protein is substituted with a basic amino acid.

5. The protein of claim 4 wherein said basic amino acid is selected from the group consisting of lysine and arginine.

6. The protein of claim 1 wherein said flavivirus envelope monomer protein has a central monomer contact interface comprising a sequence selected from the group consisting of RNQEG (SEQ ID NO: 2), GDQTR (SEQ ID NO: 3), KSQEG (SEQ ID NO: 4), KNQEG (SEQ ID NO: 5), and GDQTK (SEQ ID NO: 6).

7. The protein of claim 1 wherein said flavivirus envelope monomer protein is from a flavivirus selected from the group consisting of West Nile virus, Kunjin virus, Japanese encephalitis virus, Murray Valley encephalitis virus, dengue serotype 1 virus, dengue serotype 2 virus, dengue serotype 3 virus, dengue serotype 4 virus, yellow fever virus, tick-borne encephalitis virus, Powassan virus, and Omsk hemorrhagic fever virus.

8. The protein of claim 1 wherein said flavivirus envelope monomer protein is from a West Nile virus.

9. A polynucleotide encoding for the flavivirus envelope monomer protein of claim 1.

10. A vector comprising the polynucleotide of claim 9.

11. A host cell comprising the vector of claim 10, wherein said host cell is not in a human body.

12. An attenuated flavivirus expressing the flavivirus protein of claim 1.

13. The attenuated flavivirus of claim 12, wherein said flavivirus is selected from the group consisting of West Nile virus, Kunjin virus, Japanese encephalitis virus, Murray Valley encephalitis virus, dengue serotype 1 virus, dengue serotype 2 virus, dengue serotype 3 virus, dengue serotype 4 virus, yellow fever virus, tick-borne encephalitis virus, Powassan virus, and Omsk hemorrhagic fever virus.

14. An immunogenic composition comprising the attenuated flavivirus of claim 12.

15. The attenuated flavivirus of claim 12 which is a chimeric flavivirus.

16. The attenuated flavivirus of claim 12, wherein the flavivirus also has one or more envelope protein mutations in amino acid residues corresponding to West Nile virus envelope protein amino acids selected from the group consisting of amino acids 107, 138, 176, 177, 224, 264, 280, 316, and 440.

17. The immunogenic composition of claim 14 further comprising an adjuvant.

18. A method for inducing an immune response in a patient comprising:
  obtaining the immunogenic composition of claim 14;
  administering said immunogenic composition to the patient.

19. The method of claim 18 wherein the patient is a human.

20. The method of claim 18 wherein the administering is intravenous, intramuscular, intraperitoneal, or subcutaneous.

21. A recombinant genetic construct for encoding the flavivirus of claim 12.

22. The recombinant genetic construct of claim 21 further comprising a vector.

23. The recombinant genetic construct of claim 22 wherein said vector is a plasmid that comprises DNA encoding an infectious (+) RNA molecule under the control of a eukaryotic promoter.

24. The recombinant genetic construct of claim 23 wherein said eukaryotic promoter comprises a CMV promoter.

25. A host cell stably or transiently transfected with the recombinant genetic construct of claim 21, wherein said host cell is not in a human body.

26. An immunogenic composition comprising the recombinant genetic construct of claim 21.

27. A method for inducing an immune response in a patient comprising:
obtaining the immunogenic composition of claim 26;
administering said immunogenic composition to the patient.

28. The method of claim 27 wherein the patient is a human.

29. The method of claim 27 wherein the administering is intravenous, intramuscular, intraperitoneal, or subcutaneous.

30. A flavivirus envelope monomer protein from a tick-borne virus capable of forming a dimer along a central monomer contact interface, said flavivirus envelope protein having a central monomer contact interface sequence corresponding to amino acids 256 to 260 of the West Nile virus envelope protein, and wherein said flavivirus envelope protein has a mutation in the central monomer contact interface in which the amino acid corresponding to amino acid 260 of the West Nile virus envelope protein is substituted with a basic amino acid, which decreases dissociation of the dimer relative to a wild type sequence.

31. The protein of claim 30 wherein said basic amino acid is selected from the group consisting of lysine and arginine.

32. A flavivirus envelope monomer protein from a mosquito-borne virus capable of forming a dimer along a central monomer contact interface, said flavivirus envelope protein having a central monomer contact interface sequence corresponding to amino acids 256 to 260 of the West Nile virus envelope protein, and wherein said flavivirus envelope protein has a mutation in the central monomer contact interface in which the amino acid corresponding to amino acid 256 of the West Nile virus envelope protein is substituted with lysine, which decreases dissociation of the dimer relative to a wild type sequence.

33. A flavivirus envelope monomer protein capable of forming a dimer along a central monomer contact interface, said flavivirus envelope protein having a central monomer contact interface sequence corresponding to amino acids 256 to 260 of the West Nile virus envelope protein, wherein said flavivirus envelope monomer protein has a central monomer contact interface comprising a sequence selected from the group consisting of RNQEG (SEQ ID NO: 2), GDQTR (SEQ ID NO: 3), KSQEG (SEQ ID NO: 4), KNQEG (SEQ ID NO: 5), and GDQTK (SEQ ID NO: 6).

* * * * *